US006177283B1

(12) United States Patent
Ray

(10) Patent No.: US 6,177,283 B1
(45) Date of Patent: Jan. 23, 2001

(54) DIAGNOSTIC ASSAY

(75) Inventor: Robert A. Ray, Stuart, FL (US)

(73) Assignee: FlexSite Diagnostics, Inc., Palm City, FL (US)

( * ) Notice: Under 35 U.S.C. 154(b), the term of this patent shall be extended for 0 days.

(21) Appl. No.: 09/086,335

(22) Filed: May 28, 1998

Related U.S. Application Data
(60) Provisional application No. 60/047,982, filed on May 28, 1997.

(51) Int. Cl.[7] .......................... G01N 31/00; G01N 33/48; G01N 33/544; A01N 1/02; C12M 1/00
(52) U.S. Cl. .............................. 436/530; 436/14; 436/18; 436/63; 436/66; 436/67; 436/518; 436/826; 436/174; 436/175; 436/176; 436/177; 436/178; 435/2; 435/287.1; 435/805; 435/810; 422/56; 422/57; 422/58; 422/61
(58) Field of Search .................................. 436/14, 18, 63, 436/66, 67, 174–178, 826, 518, 530; 435/2, 810, 207.1, 805; 422/56, 61, 58, 57

(56) References Cited

U.S. PATENT DOCUMENTS

| | | | |
|---|---|---|---|
| 4,142,857 | * 3/1979 | Acuff ...................................... | 23/230 |
| 4,277,249 | 7/1981 | Broughton . | |
| 4,299,812 | 11/1981 | Coombes . | |
| 4,463,098 | * 7/1984 | Hoberman ............................. | 436/67 |
| 4,491,012 | * 1/1985 | Peterson ................................ | 73/61.4 |
| 4,649,122 | * 3/1987 | Lee ........................................ | 436/67 |
| 4,753,776 | * 6/1988 | Hillman et al. ...................... | 422/101 |
| 4,774,192 | * 9/1988 | Terminiello et al. ................ | 436/530 |
| 4,790,979 | 12/1988 | Terminiello . | |
| 4,816,224 | * 3/1989 | Vogel et al. ........................... | 422/55 |
| 4,876,069 | * 10/1989 | Jochimsen ............................. | 422/73 |
| 4,906,439 | * 3/1990 | Grenner ................................. | 422/56 |
| 5,039,493 | * 8/1991 | Oprandy ................................ | 422/101 |
| 5,135,719 | * 8/1992 | Hillman et al. ...................... | 422/101 |
| 5,149,622 | 9/1992 | Brown et al. . | |
| 5,204,267 | * 4/1993 | Sangha et al. ........................ | 436/14 |
| 5,206,144 | * 4/1993 | Zeuthen et al. ...................... | 435/7.25 |
| 5,252,489 | * 10/1993 | Macri ..................................... | 436/87 |
| 5,415,758 | * 5/1995 | Comeau ................................ | 204/299 |
| 5,415,994 | * 5/1995 | Imrich et al. ......................... | 435/5 |
| 5,416,026 | * 5/1995 | Davis ..................................... | 436/66 |
| 5,427,953 | * 6/1995 | Yee ........................................ | 436/74 |
| 5,432,097 | * 7/1995 | Yourno ................................. | 436/175 |
| 5,460,057 | * 10/1995 | Ostrup .................................. | 73/864.81 |
| 5,496,626 | * 3/1996 | Hamajima et al. ................. | 428/284 |
| 5,508,200 | * 4/1996 | Tiffany et al. ........................ | 436/44 |
| 5,516,487 | * 5/1996 | Rosenthal et al. ................... | 422/55 |
| 5,520,041 | 5/1996 | Haswell . | |
| 5,558,834 | * 9/1996 | Chu et al. ............................. | 422/55 |
| 5,599,433 | * 2/1997 | Keo et al. ............................. | 204/451 |
| 5,631,140 | * 5/1997 | Kobold et al. ....................... | 435/23 |
| 5,709,699 | * 1/1998 | Warner ................................. | 606/181 |
| 5,759,866 | * 8/1998 | Machida et al. ..................... | 436/518 |
| 5,830,170 | * 11/1998 | Whiteman et al. .................. | 604/1 |
| 5,869,345 | * 2/1999 | Chandler .............................. | 436/514 |
| 5,877,025 | * 3/1999 | Edwards et al. .................... | 436/67 |
| 5,895,704 | 4/1999 | Lerch et al. . | |
| 5,916,538 | * 7/1999 | Kohno et al. ........................ | 424/9.1 |
| 5,932,480 | * 8/1999 | Maruo et al. ........................ | 436/66 |

OTHER PUBLICATIONS

Niederau, et al., Evaluation of a Non–Liquid Transportable Device for Capillary Blood Suitable for HbA1c Determination, Clin. Chem. 42(6): 167, Abstract 0297 (1996).

Little, et al., Filter Paper Collection of Blood for Measurement of HbA1c Immunoassay, Clin. Chem. 42(6): 193, Abstract 0404 (1996).

Marsden, et al., The Comparative Performances of Whatman BFC 180 and S&S 903 Filter Papers in Newborn Screening Assays for Immunoreactive Trypson, 17–OHP and Galactose, Third Meeting of the International Society for Neonatal Screening and the 12th National Neonatal Screening Symposium, Boston, Massachusetts (Oct. 21–24, 1996).

Vohra, et al., Efficacy of New Filter Paper in a State Newborn Screening Program, Third Meeting of the International Society for Neonatal Screening and the 12th National Neonatal Screening Symposium, Boston, Massachusetts (Oct. 21–24, 1996).

Duddy, et al., The Evaluation of Whatman BFC180 Blood Collection Paper Against Two Alternative Products, Third Meeting of the International Society for Neonatal Screening and the 12th National Neonatal Screening Symposium, Boston, Massachusetts (Oct. 21–24, 1996).

Guthrie, R. et al., A Simple Phenylalanine Method for Detecting Phylketonuria in Large Populations of Newborn Infants, Pediatrics 32(3): 338–343 (1963).

Eross, J., et al., Colorimetric measurement of glycosylated protein in whole blood, red blood cells, plasma and dried blood, Ann. Clin. Biochem, 21: 477–483 (1984).

Little, et al., Collection of Blood on Filter Paper for Measurement of Glycated Hemoglobin by Affinity Chromatography, Clin. Chem. 42(5): 869–871 (1986).

Voss, et al., Stability and Accuracy Evaluation of a Capillary Collection System for Hemoglobin A1c Specimens, Clin. Chem. 37(6): 988, Abstract 0373 (1991).

Jeppsson, et al., Capillary Blood on Filter Paper for Determination of HbA1c by Ion Exchange Chromatography, Diabetes Care 19(2): pp. 142–145 (1995).

Voss, et al.; Evaluation of Capillary Collection System for HbA1c Specimens, Diabetes Care 15(5): 700–701 (1992).

* cited by examiner

Primary Examiner—Long V. Le
Assistant Examiner—Pensee T. Do
(74) Attorney, Agent, or Firm—Akerman Senterfitt & Eidson, P.A.

(57) ABSTRACT

For blood or other physiological fluid sample collection kits that use filter paper to collect the sample, the performance of the kit and associated analytical method can be improved by using a material having properties which are superior to those of standard filter paper or modified filter paper routinely used in standard biological assays. Certain materials currently available for uses other than blood collection, storage, or transport have properties that are advantageous as employed in assays of biological fluids, including the use of specific cellulose blotting materials for collecting blood samples for hemoglobin or hemoglobin A1c monitoring.

12 Claims, No Drawings

DIAGNOSTIC ASSAY

CROSS-REFERENCE TO RELATED APPLICATIONS

This application claims priority from provisional patent application, Ser. No. 60/047,982, filed on May 28, 1997.

FIELD OF THE INVENTION

This invention relates to the general area of remote site blood sample collection for medical diagnostic tests. More specifically, the invention relates to medical diagnostic tests using filter paper to collect the blood sample.

DISCUSSION OF THE RELEVANT ART

Historically, blood samples have been drawn from a patient in a hospital or physician's office using an evacuated test-tube to collect blood from a venipuncture by a physician, nurse, or other medical professional. Alternatively, a method for sampling of blood at a site remote from the hospital, physician's office, or laboratory has developed over the years where a small amount of blood may be obtained from a fingerstick and the blood can be absorbed onto filter paper to collect the sample. This is known in the art as a "dry" technique, as opposed to a "wet" remote site sampling technique that involves collection of a blood sample in a capillary tube.

Dry remote site blood spot sampling had its beginning in the 1960's with the use of filter paper to gather blood spot samples from neonates for use in the determination of the presence of phenylketones (Guthrie, et al., [1963] *Pediatrics* 32(3): 338–343). Since that time, a number of products have been introduced that are designed to facilitate remote site sample collection and transport of the sample to a laboratory for analysis. The availability of remote site blood collection such that the collected sample can be transported to a laboratory for analysis has been very successful in monitoring blood components of diabetics.

Diabetes is a chronic and serious disease which affects over 100 million individuals worldwide. In the United States, there are 8 million diagnosed cases of diabetes, with an estimated 8 million cases undiagnosed. Diabetes is the leading cause of blindness, stroke, kidney failure, and amputations in the U.S. Because a person with diabetes is ten (10) times more likely to require hospitalization than the general population, the direct and indirect medical costs for treating diabetes have been estimated to exceed $105 billion annually. This total equals 14.6% of total U.S. health care expenditures being consumed by 3% of the population.

In about 1980, Schleicher and Schuell Corp. (S&S) began producing a filter paper attachable to a test request form (designed to order). In using the S&S system, a blood spot is placed in one or more designated areas of the filter paper, allowed to dry, and then mailed along with the test request form to the laboratory.

Eross, et al. introduced the use of filter paper spots for the gathering of blood spot samples for the measurement of glycohemoglobin. Eross, et al. (1984) Ann. Clin. Biochem. 21: 477–483. In 1986 Little, et al. reported on the use of filter paper blood spotting for measuring glycohemoglobin by affinity chromatography (Little, et al., [1986] Clin. Chem. 32(5): 869–871). Measurement of glycosylated hemoglobin (glycohemoglobin) or a component thereof, e.g., HbA1c, is extremely important in metabolic control of diabetics. Using the Little technology, Evalu-lab, a subsidiary of Awareness Technology, produced a product, Self-Assure™ (now owned by FlexSite Diagnostics), between 1987 and 1992 which gathered a blood spot sample on filter paper for glycohemoglobin or HbA1c determination. The blotting material used in these assays was a glucose oxidase-treated filter paper.

The methods and materials in this art have been the subject of many patents, including U.S. Pat. No. 5,516,487, which describes the use of various antibiotics or preservatives in combination with a cotton fiber filter paper, as well as the use of multiple application zones on the filter paper which are isolated from each other by perforations in the filter paper; U.S. Pat. No. 5,508,200, which describes the use of S&S 903 and S&S 470 filter papers in a complex integrated analytical system and measurement of chemical reactions on the filter paper matrix; U.S. Pat. No. 5,432,097, concerning digestion of the filter paper with cellulase so that recovery of intact cells can be achieved; U.S. Pat. No. 5,427,953, which concerns measurement of a heavy metal (e.g., lead) from blood samples collected on filter paper; U.S. Pat. No. 5,204,267, which describes preservation of blood samples collected on various filter matrices for glucose analysis; U.S. Pat. No. 4,816,224, which is directed to a multiple layer device for separating plasma or serum from a blood sample collected for glucose analysis; U.S. Pat. No. 4,299,812, pertaining to an improved thyroid function (T4) test; and U.S. Pat. No. 4,227,249, which primarily concerns a drying procedure and its effect on the results of an assay measuring somatomedin. The disclosures of these patents are hereby incorporated by reference.

Other patents describing the use of certain blotting materials used in biological assay methods include U.S. Pat. Nos. 5,496,626; 5,460,057; 5,415,758; 4,790,797; and 4,774,192. None of the above-referenced patents relate to the use of blotting materials used in association with a standard assay for hemoglobin (Hb) or hemoglobin A1c (HbA1c) or describe superior performance of the Hb or HbA1c assay by use of those materials.

In about 1992, Bio-Rad introduced a 100 test kit (wet samples) to facilitate the collection of capillary samples for analysis on their Diamat™ HPLC (High Performance Liquid Chromatography) system. Eli Lilly subsequently packaged a one test version of this kit as a promotional tool for their insulin products.

In Sweden about 1994 Boehringer Mannheim Corp. (BMC) introduced a mail-in, filter paper based ("dry") blood spot kit under the name of "Via Post™" for HbA1c measurement. This BMC kit was evaluated by Jeppsson, et al. (Diabetes Care 19(2): pp. 142–145). BMC also introduced a "wet" capillary HbA1c kit for analysis on a Bio-Rad HPLC in 1995, and in 1996 introduced a screen material for blood spot sampling for analysis with their TinaQuant™ method for Hemoglobin A1c (Niederau, et al. [1996] Clin. Chem. 42(6): 167). Little, et al. ([1996] Clin. Chem. 42(6): 193) evaluated the use of filter paper for HbA1c sample collection with analysis by HPLC and by the Roche Unimate™ method Voss, et al. evaluated capillary collection systems for HbA1c analyses. Diabetes Care (1992) 15: 700.

Historically, the most commonly used material for these assays has been S&S 903, a cotton linter paper. However, certain disadvantages have been associated with the S&S 903 paper and its equivalents available from other manufacturers, e.g., Whatman. Specifically, certain of these commercially available and commonly used materials lack characteristics which provide precision values and accuracy that is preferred for carrying out a commercially superior HbA1c assay.

Measurement of HbA1c, unlike blood glucose monitoring which provides an individual with their glucose value at that instant, measures the degree of diabetes control over the last 2–3 month period. In doing so, HbA1c monitoring provides the health care professional and patient a critical tool to determine the effectiveness of the patient's therapy and/or the patient's overall compliance.

Albeit recognized that HbA1c monitoring is beneficial, it is estimated that fewer than 16% of the 8 million individuals with diabetes have an A1c test annually, less than 10% have the test performed on a quarterly basis as recommended. The primary reasons for this is that a majority of patients with diabetes are treated by primary care physicians who are not current on the benefits of intensive therapy and HbA1c monitoring. Also, A1c testing has historically been an expensive laboratory test which required a blood draw by venipuncture which is poorly tolerated by both young and older patients.

Thus, discovery of unexpectedly improved or superior Hb or HbA1c assay results using materials that are commercially available and presumed to provide only equivalent results adds significantly to this art by improving the accuracy of detection of the blood components of interest. Improved accuracy of detection can contribute to more precise monitoring and overall better health care and quality of life for the patients who may rely on these assays to monitor glycohemoglobin.

SUMMARY OF THE INVENTION

It is an object of the invention to provide an improved assay for measuring or detecting a component of interest in a biological fluid, e.g., blood.

It is another object of the invention to provide an improved assay method or an article of manufacture for detecting or measuring hemoglobin A1c (HbA1c) in a biological fluid.

It is a further object of the invention to provide a kit having particular unexpected advantages for measuring or detecting a component of interest in a biological sample, e.g., HbA1c in blood.

The subject invention thus concerns a system which can provide an improvement, e.g., superior performance, in a standard assay for measuring HbA1c. Specifically, the improved performance results from the utilization as a blotting material of a particular membrane or filter product made from natural or synthetic materials or composites. The material selected for use in accordance with the subject invention, e.g., the cellulose filter paper, Ahlstrom 319, which is commercially available, advantageously exploits one or more properties that can give improved performance characteristics such as assay precision, sample stability, accuracy of quantitative or qualitative detection, ease of sample handling, and the like. Certain materials according to the subject invention can provide improved precision or other advantages as compared to the commonly used S&S 903 cellulose filter paper as a blotting material. Improved precision or other such performance characteristics can result in superior product performance. Improving the procedure of measuring or detecting HbA1c so that the precision of the HbA1c assay has a within-run precision coefficient of variation (CV) less than 2%, as provided by the subject invention, can be commercially significant and advantageous.

DETAILED DESCRIPTION OF THE INVENTION

The subject invention concerns an advantageous system for detecting or measuring a component of interest in a biological sample. For example, the system according to the instant invention includes the use of a particular blotting material for collection of a blood specimen for assaying the presence or amount of a component that is present in or absent from the blood of a patient being tested for that component. In a preferred embodiment, the invention concerns the use of a particular blotting or "blood spotting" material in a method article of manufacture, or kit for determining concentrations of hemoglobin A1c in the blood of a patient. In a most preferred embodiment, the blotting material comprises a single layer of material. A plurality of distinct layers of materials can also be used in accordance with the subject invention. For example, certain laminations can be included to achieve separation of certain components, e.g., red blood cells, in a blood sample.

Certain properties or characteristics of the blotting materials have shown unexpected improvements in biological assays as compared to commonly used blotting materials, e.g. S&S 903. The advantageous properties include: ability to absorb blood quickly and neatly, release of protein readily during elution, reproducibility of protein elution, spot diameter, spot appearance, wet strength, and ability to be punched, or "punchability".

Several categories of blotting materials for blood specimen collection are available. These include: cellulose (wood or cotton derived), glass fiber, glass fiber/cellulose composites, nylon, modified polyester, polypropylene, nitrocellulose, modified polyethersulfone, polyvinylidene fluoride, modified natural and synthetic fibers, laminated materials, and screens. From more than 100 materials evaluated with regard to their properties for blood spot collection and recovery, we have discovered that the use of certain membranes or filter materials as a blotting material for gathering, storing and/or transporting a physiological fluid, e.g., blood, can facilitate or improve the capabilities of measuring hemoglobin (Hb) or hemoglobin A1c (HbA1c).

One requirement for a material that can be used in accordance with the subject invention is its ability to absorb blood readily and quickly. Many of the materials examined do not. A second property of a material used in accordance with the subject invention is its ability to release the components of interest, e.g., hemoglobin and hemoglobin A1c, that has been absorbed into or onto the blotting material. In a preferred embodiment, the material used can release the component of interest efficiently and precisely. That is, the material itself should minimally affect measurement or detection of the component of interest. In general, the better the precision of the hemoglobin elution, the better the precision of the HbA1c measurement. Thus the most favorable materials provide high Hb recovery, low coefficient of variation (CV) for Hb precision, and low coefficient of variation (CV) for HbA1c precision.

One preferred material is a cellulose (cotton fiber) filter paper, Ahlstrom 319, which has a low precision characteristic and a low CV for the hemoglobin measurement. It also gives a spot with a good appearance and is easy to punch after drying. The hemoglobin recovery is relatively low compared with other cotton fiber filter papers, but this does not seem to hurt the performance in the critical area of precision of HbA1c measurement. Another preferred material is Ahlstrom 205. Its performance mirrors that of Ahlstrom 319 and can give slightly higher hemoglobin recovery than Ahlstrom 319. It would be understood by those of ordinary skill in the art that the blotting material can be treated, e.g., with enzymes, enzyme inhibitors, or other chemicals, to achieve certain results in accordance with the assay being conducted. Both of these filter materials, Ahlstrom 319 and Ahistrom 205 are commercially available from Ahlstrom Filtration, Inc., Mt. Holly Springs, Pa.

In one embodiment of the invention, the blotting material can be included as part of a kit for remote site blood sampling. The kit can comprise a blotting material having at least one designated area for placing a blood drop, a sterile lancet commonly used for obtaining a finger prick blood sample, instructions for use of the kit, and a sealable container, e.g., a plastic bag suitable for containing a biological sample. The preferred embodiment of the kit of the subject invention can include Ahlstrom 319 or Ahlstrom 205 as the blotting material. The kit can further comprise a return mailer, with instructions for transmitting the sample to the laboratory for analysis. Other components, as would be readily recognized by those of ordinary skill in the art, can also be included as part of the kit.

Following are examples which illustrate procedures for practicing the invention. These examples should not be construed as limiting. All percentages are by weight and all solvent mixture proportions are by volume unless otherwise noted.

Example 1—Precision of S&S 903 filter paper:

Spot-to-spot precision of S&S 903 paper was determined by spotting five spots of EDTA antimicrobial-coagulated blood from three patients (low, medium, or high percent of HbA1c) on cards made of the blotting material of interest, drying overnight, placing the cards in plastic bags and storing at room temperature, eluting the spots on the day noted and assaying the eluate on the Roche Cobas Mira to determined HbA1c percentage in the blood of the patient. The results are shown below in Table 1.

TABLE 1

SPOT-TO-SPOT PRECISION OF PERCENTAGE OF HbA1c MEASUREMENTS USING S & S 903

| Sample | | Result 1 | 2 | 3 | 4 | 5 | Mean | s.d. | CV % |
|---|---|---|---|---|---|---|---|---|---|
| Low | day 2 | 6.5 | 6.9 | 6.9 | 6.9 | 6.6 | 6.5 | 0.17 | 2.6 |
| (5–7% HbA1c) | day 4 | 6.7 | 6.4 | 6.5 | 6.4 | 6.6 | 6.5 | 0.12 | 1.8 |
| | day 6 | 6.6 | 6.4 | 6.7 | 6.4 | 6.3 | 6.5 | 0.15 | 2.3 |
| | day 9 | 6.5 | 6.4 | 6.4 | 6.4 | 6.9 | 6.5 | 0.19 | 3.0 |
| | day 11 | 6.6 | 6.4 | 6.5 | 6.4 | 6.6 | 6.5 | 0.09 | 1.4 |
| Medium | day 2 | 8.5 | 8.0 | 8.6 | 8.7 | 8.4 | 8.4 | 0.24 | 2.9 |
| (7–9% HbA1c) | day 4 | 8.3 | 8.0 | 8.3 | 8.2 | 8.8 | 8.3 | 0.26 | 3.2 |
| | day 6 | 8.0 | 7.8 | 7.9 | 8.4 | 8.0 | 8.0 | 0.20 | 2.5 |
| | day 9 | 8.0 | 8.6 | 8.5 | 8.0 | 8.6 | 8.3 | 0.37 | 4.3 |
| | day 11 | 8.1 | 8.6 | 8.2 | 8.7 | 8.3 | 8.4 | 0.23 | 2.8 |
| High | day 2 | 12.4 | 12.6 | 12.0 | 12.4 | 12.5 | 12.4 | 0.20 | 1.7 |
| (10–15% HbA1c) | day 4 | 12.4 | 12.9 | 12.7 | 12.7 | 12.4 | 12.6 | 0.19 | 1.5 |
| | day 6 | 12.1 | 12.7 | 12.8 | 13.0 | 12.6 | 12.6 | 0.30 | 2.4 |
| | day 9 | 13.2 | 12.8 | 13.3 | 12.6 | 13.0 | 13.0 | 0.26 | 2.0 |
| | day 11 | 13.3 | 12.9 | 13.8 | 13.2 | 13.6 | 13.6 | 0.31 | 2.4 |

The median coefficient of variation (CV), which is a measurement of precision of the assay, is at least about 2.5% for measurement of HbA1c using S&S 903 filter paper as a blotting material. However, the range of CV's is 1.4–4.5% more than 46% of all runs have a CV in excess of 2.5%.

These precision values were measured at HbA1c levels in the normally encountered range (typically 5–15% HbA1c).

Example 2—Properties of other blotting materials:

While S&S 903 has been utilized rather extensively for many years as a means to gather and transport blood samples, we have discovered certain materials which offer better performance in one or more properties. The precision of the materials studied for better performance was also determined by measuring the spot-to-spot variability of five spots. The reproducibility of the performance of a given material was determined by repeating a precision study several times (typically 5 or more) over a period of several days. The other properties of interest were recorded during the precision studies. Several materials have been found which advantageously have precision coefficients of variation (CV), at most below about 2.5%, and advantageously consistently below 2%. Each of the materials has the ability to readily absorb blood from a fingerstick. Table 2, below, lists the materials with performance superior to that of S&S 903.

TABLE 2

CHARACTERISTICS OF PREFERRED MATERIALS

| Mfr | Material | Composit'n | Hb | Hb CV % | HbA1c Precision CV % | Appearance | Punchability |
|---|---|---|---|---|---|---|---|
| S & S | 470 | Cellulose | 210 | 5 | 1.9, 2.2, 2.5, 2.6, 0.9 | Good | Good |
| S & S | 740E | Cellulose | 250 | 8 | 2.0, 0.0, 0.0, 1.9, 2.3 | Good | Good |
| Whatman | C/DE 30 | Cellulose | 210 | 4 | 2.1, 2.2, 1.2, 1.5, 2.0 | Good | Good |
| Whatman | 3MMchr | Cellulose | 235 | 4 | 1.5, 2.1, 1.5 | Good | Good |
| Whatman | C-5031 | Cellulose | 260 | 4 | 0.8, 1.5, 1.1, 2.1 | Good | Good |
| Ahlstrom | 205 | Cellulose | 200 | 5 | 0.9, 1.1, 1.4, 1.0 | Good | Good |
| Ahlstrom | 319 | Cellulose | 150 | 3 | 1.3, 1.4, 0.9, 1.9, 1.7 | Good | Good |
| Pail | Hemsep-L | Modified Polyester | 160 | 5 | 2.0, 1.3, 2.5, 2.8 | Good | Hard |
| Pail | Loprosorb | Modified Fiber | 320 | 8 | 2.1, 0.9, 1.1, 2.3 | Irreg | Hard |

The Hb and Hb CV values are approximate averages. Precision values are determined from five replicate spots of 20 microliters of blood applied to the material with a pipet.

All of the materials listed in Table 2 give precision performance superior to that of S&S 903 in the experiments performed. However, in combination with the other properties certain of the materials are superior in overall performance. For example, a cellulose blotting material sold as Ahlstrom 319 has a low precision characteristic and the lowest CV for hemoglobin measurement of the cellulose tested. These characteristics can provide a technical and commercial advantage for HbA1c determinations by maintaining an HbA1c precision value consistently at 2.0% or below.

I claim:

1. A method for assaying a component of interest in a biological sample, said method comprising the steps of:
   providing a blotter material comprising cellulose for absorbing a liquid aliqout of the biological sample comprising the component of interest;
   applying the liquid aliquot of the biological sample to the blotter material;
   allowing the liquid aliquot of the biological sample to dry on the blotter material to form a dried biological sample;
   eluting the component of interest from the dried biological sample; and
   assaying the component of interest in the dried biological sample to yield a datum corresponding to the quantity of the component of interest within the biological sample;
   wherein the blotter material is selected such that repetition of the method a plurality of times using additional liquid aliquots of the biological sample yields a plurality of data points corresponding to the quantity of the component of interest within the biological sample, the plurality of data points having a coefficient of variation of less than about 2.5%.

2. The method of claim 1, wherein said component of interest is glycosylated hemoglobin or a component thereof.

3. The method of claim 1, wherein said component of interest is hemoglobin A1c.

4. The method of claim 1, wherein said biological sample is blood.

5. The method of claim 1, wherein the coefficient of variation is less than about 2.0%.

6. The method of claim 1, wherein the cellulose blotter material provides at least one property selected from the group consisting of: rapid sample absorption, improved sample spot formation, improved sample stability, releasability of a component of interest during the elution step, reproducibility of elution of the component of interest, resistance to tearing when wetted, and capability of being punched.

7. The method of claim 6, wherein said improved spot formation property includes control of diameter of the spot, control of liquid edge formation of the spot, or control of cell separation from plasma or serum of the spot.

8. The method of claim 1, wherein the blotting material is a laminate.

9. The method of claim 1, wherein the steps of providing the blotter material and applying the liquid aliquot of the biological sample to the blotter material are performed at a first location; and the steps of eluting and assaying the component of interest are performed at a second location remotely located from the first location.

10. The method of claim 9, further comprising the step of mailing the blotter material from the first location to the second location after the liquid aliquot of the biological sample has been applied to the blotter material.

11. The method of claim 10, wherein the biological sample is blood.

12. The method of claim 11, wherein the component of interest is hemoglobin A1c.

* * * * *

UNITED STATES PATENT AND TRADEMARK OFFICE
CERTIFICATE OF CORRECTION

PATENT NO. : 6,177,283 B1
DATED : January 23, 2001
INVENTOR(S) : Robert A. Ray

It is certified that error appears in the above-identified patent and that said Letters Patent is hereby corrected as shown below:

Column 5,
Line 26, replace "Ahistrom" with -- Ahlstrom --,

Column 6,
Line 67, replace "have" with -- having --

Column 7,
Table 2, replace "Pail" with -- Pall --

Signed and Sealed this

Ninth Day of April, 2002

Attest:

JAMES E. ROGAN
Attesting Officer   Director of the United States Patent and Trademark Office